US005876324A

United States Patent [19]

Trouchine

[11] Patent Number: 5,876,324

[45] Date of Patent: Mar. 2, 1999

[54] PENILE STIMULATOR DEVICE USING TURBULENT WATER FLOW AND METHOD OF USE

[76] Inventor: Eugene Trouchine, 2560 Kingston Road, #607, Scarborough, Ontario, Canada, M1M 1L8

[21] Appl. No.: 937,808

[22] Filed: Sep. 25, 1997

[30] Foreign Application Priority Data

Sep. 27, 1996 [CA] Canada .................................. 2186671

[51] Int. Cl.$^{6}$ ........................................................ A61F 5/00

[52] U.S. Cl. ................................................................ 600/38

[58] Field of Search .......................... 600/38–41; 601/46; 128/842–844, 845

[56] References Cited

U.S. PATENT DOCUMENTS

| | | |
|---|---|---|
| 104,204 | 6/1870 | Rice . |
| 222,690 | 12/1879 | Goldschmidt . |
| 998,804 | 7/1911 | Salisbury . |
| 2,243,297 | 7/1941 | Taylor . |
| 2,272,481 | 2/1942 | Rinkes et al. . |
| 2,832,336 | 4/1958 | Davis et al. . |
| 3,094,983 | 6/1963 | MacLeod . |
| 3,500,832 | 3/1970 | Nunnery . |
| 4,407,275 | 10/1983 | Schroeder . |
| 5,234,401 | 8/1993 | Yamanaka ................................ 600/38 |
| 5,243,968 | 9/1993 | Byun . |
| 5,421,808 | 6/1995 | Osbon et al. . |
| 5,634,890 | 6/1997 | Morris . |

*Primary Examiner*—John P. Lacyk
*Assistant Examiner*—Samuel Gilbert

[57] ABSTRACT

The invention provides a penile stimulation device for use in the treatment of male impotence utilizing turbulent flow of fluid, the device comprising: tubular housing means, having internal walls, a closed forward end and an open rearward end, said rearward end having an opening means for encircling the penile shaft, for housing the penis submersed in fluid and disposed at a sufficient distance from said internal walls to permit fluid flow between the penis and said internal walls; and pumping means for conveying a flow of turbulent fluid between the penis and said internal walls in and out of the housing. The invention also provides a method of penile stimulation for use in the treatment of male impotence utilizing turbulent flow of fluid, the method comprising: inserting the penis into a tubular housing means, having internal walls, a closed forward end and an open rearward end, said rearward end having an opening means for encircling the penile shaft, for housing the penis submersed in fluid and disposed at a sufficient distance from said internal walls to permit fluid flow between the penis and said internal walls; and pumping a flow of turbulent fluid between the penis and said internal walls in and out of the housing.

20 Claims, 4 Drawing Sheets

PENILE STIMULATOR DEVICE USING TURBULENT WATER FLOW AND METHOD OF USE

TECHNICAL FIELD

The invention is directed to a device for penile stimulation in the treatment and prevention of male impotence utilizing the turbulent flow of water, and a method of use.

BACKGROUND OF THE ART

Many men suffer from the inability to obtain or maintain an erection. The sources of this problem are physical, psychological or a combination of both well known to medical professionals. This problem was once falsely considered as an inevitable part of aging or as such a private matter that many men suffered unnecessarily in failing to seek medical treatment.

An erection is maintained by contraction of the pubococcygeal muscle, which constrict blood vessels after the penis has become engorged with blood. The pubococcygeal muscle is also known as the PC muscle, or Housten muscle and forms a floor at the base of the pelvis much like a hammock supporting the internal organs of the body.

For women, during childbirth, the PC muscle is stretched and weakened by carrying and delivering babies. In men, the strength of the PC muscle may deteriorate through ill health, accident or through lack of use like any other muscle of the body. Failure or weakness of the male PC muscle results in escape of blood from the penis and subsequent loss of erection.

Physical rehabilitation of the PC muscle is possible through a program of regular exercise, also like any other muscle of the body. Conventional responses to this problem have only been partially successful for men. For example, an exercise known as the Kegel exercise has been used to strengthen the PC muscle and has proved to be an aid in sustaining an erection and controlling orgasm. Kegel exercises are very well known, and are regularly taught to pregnant women in childbirth classes to help ease the trauma of delivery and to shorten their recovery for example. What is less well known is the effect of this same exercise when practiced by men, likely due to the sensitive nature of the subject.

Extended contraction and repeated exercise of the PC muscle gradually builds up the muscle strength. As with any other body muscle, this gradual process does not achieve maximal efficiency unless exercise is regular, challenges the muscle tissue and is continued for a sufficient length of time. Any muscular exercise which is too strenuous actually contributes to muscle fibre deterioration, whereas an exercise program that is not challenging enough does not rehabilitate the muscle at an optimal rate of progress.

The optimal use of the Kegel exercise is difficult to monitor scientifically and establishing a medically prescribed exercise regimen is impractical. However, the benefits of regular Kegel exercise have become an accepted part of medical recovery programs for building PC muscle strength in men suffering from inability to obtain or maintain an erection, and for raising the awareness of their bodily responses in men suffering from premature ejaculation. Similar exercises are used during what is known as “tantric” sexual practices, currently raising much interest in western countries, which combine eastern mysticism, meditation, yoga breathing exercises, and include exercise of the PC muscle. In short, better control over the PC muscle results from the strengthening and awareness of this muscle through exercise. Better control leads to medically verifiable improvement in the sexual functioning of such patients.

Other exercises used in treatment involve use of devices which stimulate the penis principally through frictional engagement between the device and penis. Such devices may irritate or damage the skin especially if use is extended defeating their intended purpose when pain or discomfort is experienced by the user. In addition, the user has very little real control over the level of stimulation and certainly not to the degree of repeatability required for scientific measurement and medical treatment.

The use of exercises and stimulatory devices are not intended to result in orgasm. In fact, orgasm results in a lessening of the effectiveness of the exercises. The optimal exercise regimen includes prolonged and repeated contraction of the PC muscle. It is possible to contract and exercise the PC muscle when the penis is not erect, however, the effectiveness of the Kegel exercise is greatly enhanced if an erection is maintained during exercise by an optimal but relatively low level of stimulation.

It is desirable therefore to produce a penile stimulation device which does not produce frictional discomfort when used and can be controlled to effect maximum rehabilitation of the PC muscle through repeated exercise.

DISCLOSURE OF THE INVENTION

The invention provides a novel penile stimulation device for use in the treatment of male impotence utilizing turbulent flow of fluid, the device comprising: tubular housing means, having internal walls, a closed forward end and an open rearward end, said rearward end having an opening means for encircling the penile shaft, for housing the penis submersed in fluid and disposed at a sufficient distance from said internal walls to permit fluid flow between the penis and said internal walls; and pumping means for conveying a flow of turbulent fluid between the penis and said internal walls in and out of the housing.

Also in accordance with the invention is provided a method of penile stimulation for use in the treatment of male impotence utilizing turbulent flow of fluid, the method comprising: inserting the penis into a tubular housing means, having internal walls, a closed forward end and an open rearward end, said rearward end having an opening means for encircling the penile shaft, for housing the penis submersed in fluid and disposed at a sufficient distance from said internal walls to permit fluid flow between the penis and said internal walls; and pumping a flow of turbulent fluid between the penis and said internal walls in and out of the housing.

The use of flowing fluid, such as warm bath water for example, produces a gentle stimulation without abrasive friction. The level of stimulation is controlled through the use of valves to control flow and with turbulence inducing corrugations in the housing. The gentle stimulation provokes and maintains an erection longer and in a firmer state than with frictional devices thereby providing a more regulated, repeatable, and extended exercise program for the deteriorated PC muscle.

Further details of the invention and its advantages will be apparent from the detailed description and drawings included below.

BRIEF DESCRIPTION OF THE DRAWINGS

In order that the invention may be readily understood, two preferred embodiments of the invention and variations thereof will be described by way of example, with reference to the accompanying drawings wherein.

DETAILED DESCRIPTION OF PREFERRED EMBODIMENTS

Figure 1:
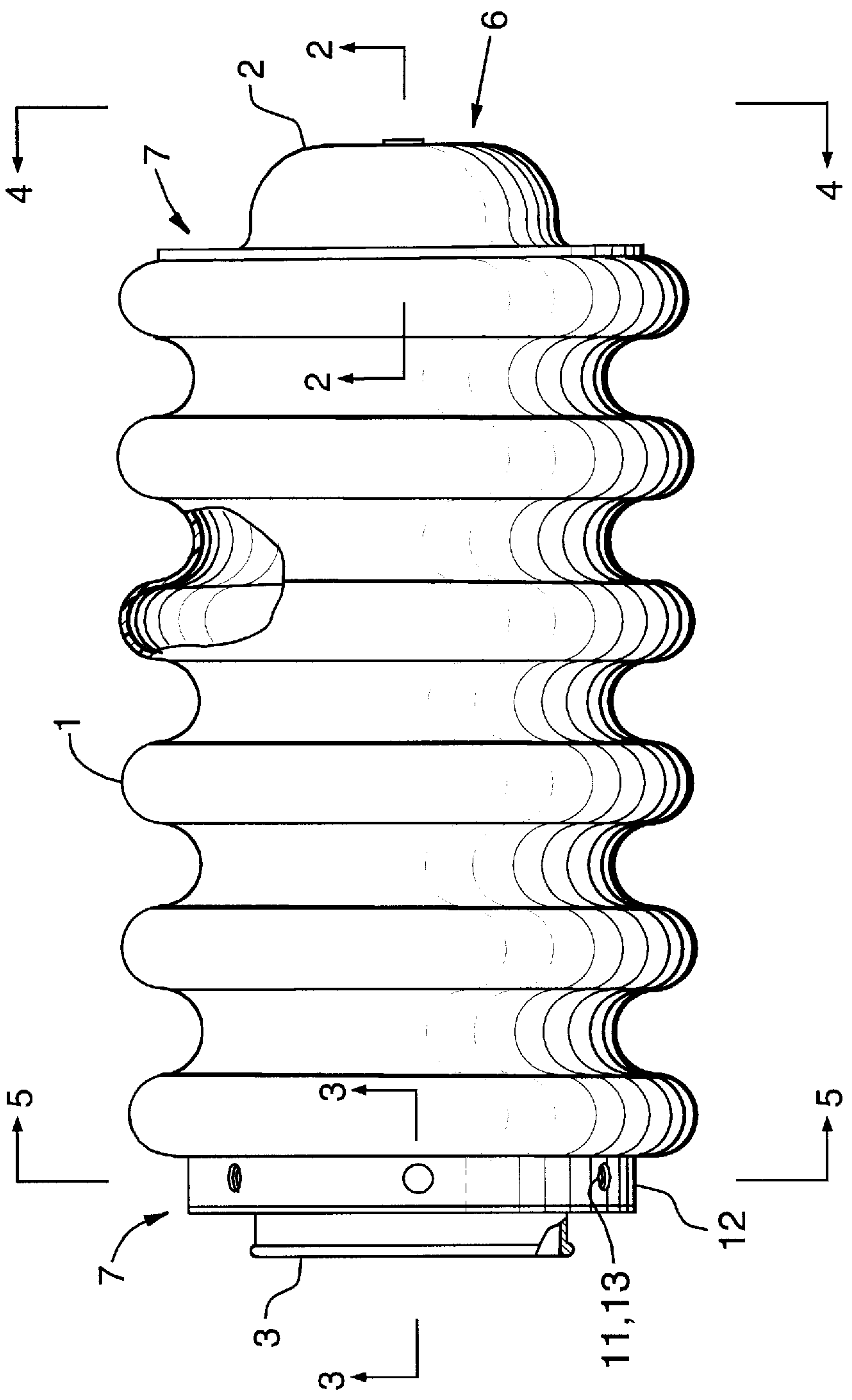
FIG. 1 is side view of a manually operable penile stimulator device, drawn with the open rearward end to the right.

With reference to FIG. 1, the a manually operated embodiment of the invention is illustrated. It will be understood that various means to produce a flow of turbulent water are within the contemplation of the invention, however, it is considered most likely that the commercial embodiment will be a simple inexpensive manually operated device as illustrated.

The device generally comprises a tubular housing I preferably of flexible plastic or rubber. The illustrated embodiment has corrugated walls internally and externally forming a bellows type of structure. The tubular housing I has a closed forward end 2 and an open rearward end 3.

Figure 3:
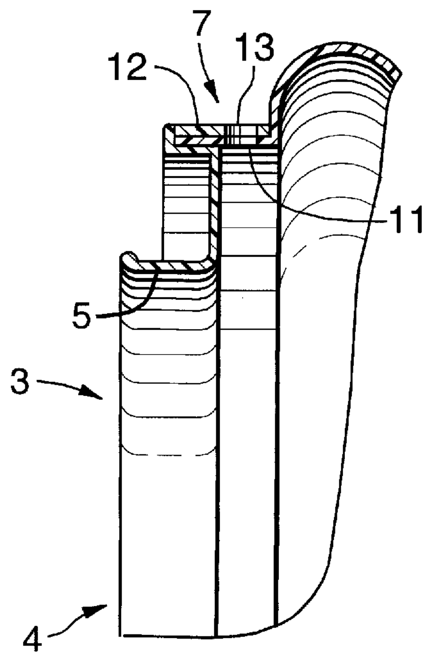
FIG. 3 is a detail sectional view of the rearward end along lines 3—3 of FIG. 1 showing one type of outlet valve with apertures through the housing and a sliding ring for selectively regulating fluid flow.

As shown in FIG. 3, the rearward end 3 has an opening 4 for encircling the penile shaft. Preferably the opening 4 is formed with a removable annular bushing 5 to accommodate various sizes and to sealingly engage the shaft.

The tubular housing 1 houses the penis submersed in fluid and disposed at a sufficient distance from the internal walls of the housing to permit fluid flow between the penis and the internal walls. Manual or mechanical pumping means are provided for conveying a flow of turbulent fluid between the penis and the internal walls in and out of the housing 1.

To use the device, the user inserts his penis through the opening 4 in the flexible bushing 5. The user sits in a bath of warm water thereby submersing the housing 1. Where the housing 1 comprises a flexible bellows as illustrated, fluid is pumped manually through reciprocal axial movement of the housing 1 relative to the penis.

Figure 6:
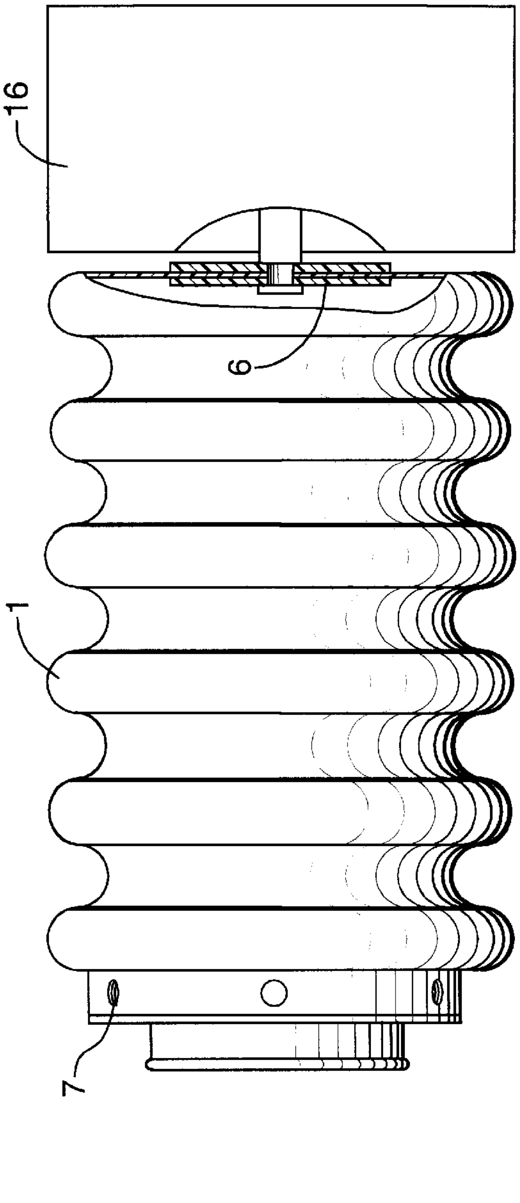
FIG. 6 is a side view of a second embodiment including mechanical pumping means in the form of a vibrator.

Any suitable pumping means can include means to regulate fluid flow. In the manual embodiment illustrated, the regulating means comprise a housing inlet 6 and outlets 7. The inlet 6 comprises a simple one way check valve, as shown in FIGS. 2 and 6, having a radially spaced ring of inlet apertures 8 and a flexible valve washer 9 secured to the forward end 2 with a rivet 10.

Figure 2:
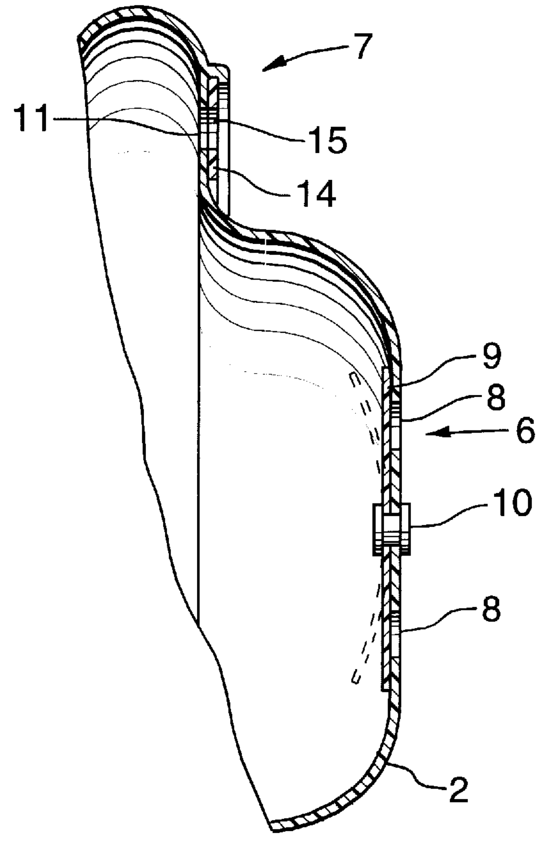
FIG. 2 is a detail sectional view of the forward end along lines 2—2 of FIG. 1 showing the one way inlet check valve coaxial to the device centreline.

As shown in dashed outline in FIG. 2, the flexible washer 9 deforms and folds inwardly when pressure inside the housing 1 is less than the pressure outside of the housing 1, i.e.: on expansion of the bellows like housing 1. When pressure inside the housing 1 is greater than the pressure outside the housing 1, i.e.: on compression of the housing 1, the washer 9 is compressed against the forward end 2 sealing the inlet aperture 8. In such a condition, the fluid escapes from the outlets 7.

Two types of fluid outlets 7 are shown both comprising a series of outlet apertures 11 and gate means for selectively impeding fluid flow through the outlet apertures 11. Firstly referring to FIGS. 3, and 1, a rearward outlet 7 has a plurality of outlet apertures 11 disposed radially through the housing 1 adjacent the rearward end 3 of the housing 1. The gate means comprise a sliding ring 12 fitted in a groove in the rearward end 3 and having an associated plurality of ring apertures 12. By selectively positioning the ring 12 radially relative to the rearward end 3 of the housing 1, the water flow through the apertures 11, and 13 can be controlled.

Figure 4:
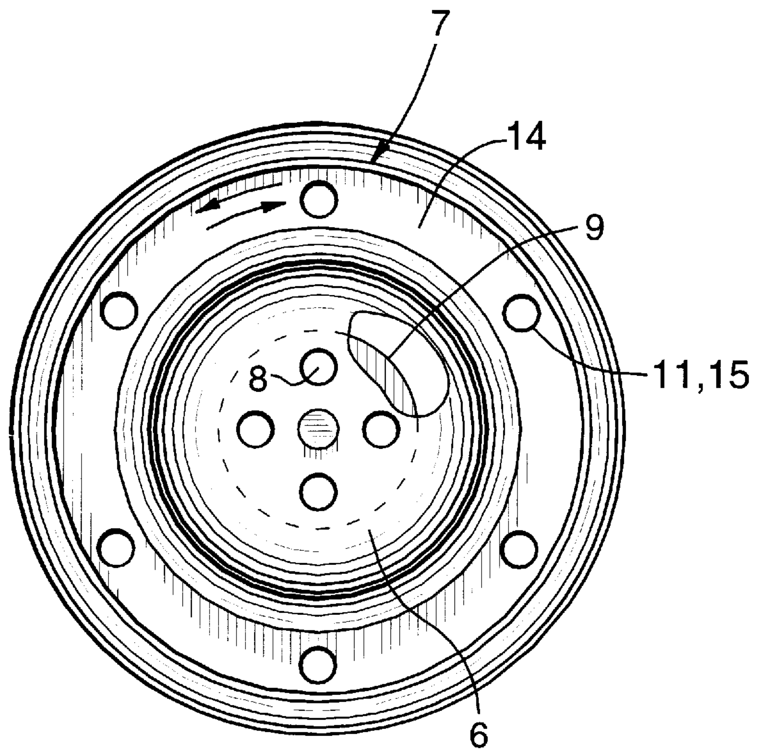
FIG. 4 is an end view of the forward end along lines 4—4 of FIG. 1.
Figure 5:
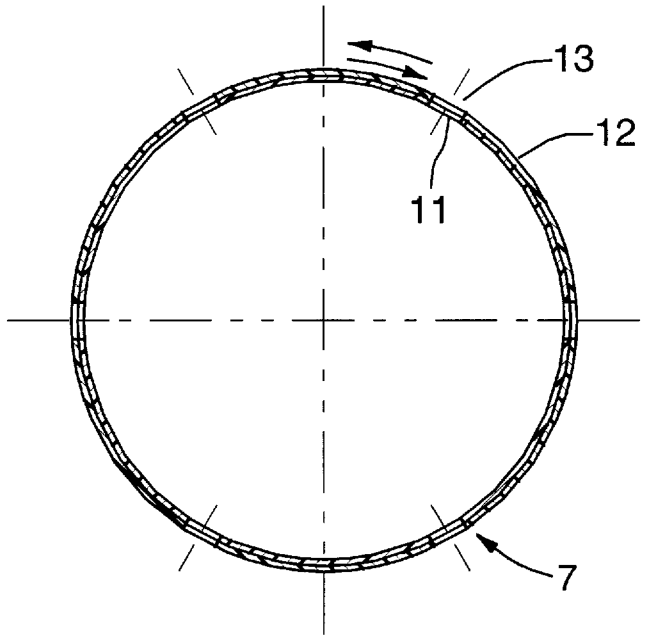
FIG. 5 is a sectional view of the rearward end along lines 5—5 of FIG. 1.

Secondly referring to FIGS. 4 and 2, a forward outlet 7 has a plurality of outlet apertures 11 disposed radially through the forward end 2 of the housing 1. The gate means comprise a sliding disk 14 fitted in an annular groove in the forward end 2 and having an associated plurality of disk apertures 14. By selectively positioning the disk 14 radially relative to the forward end 2 of the housing 1, the water flow through the apertures 11, and 115 can be controlled.

Preferably the internal walls of the housing 1 are corrugated to increase fluid turbulence which aids in providing stimulation. As shown in FIG. 1, a bellows type housing 1 is corrugated for flexible axial movement and such annular corrugations also enhance turbulence.

It is within the contemplation of the invention to provide mechanically operable pumping means and in such a case the housing may include various corrugations to increase turbulence without requiring the housing to be flexible. For example a small electric pump could be attached to the inlet to produce fluid flow. As shown in FIG. 6 mechanically operable pumping means can also include vibrating means 16. In the embodiment illustrated, the vibrator 16 produces axial reciprocal movement of the bellows housing 1 thereby mechanically pumping fluid in the inlet 6 and out the outlet 7.

Figure 7:
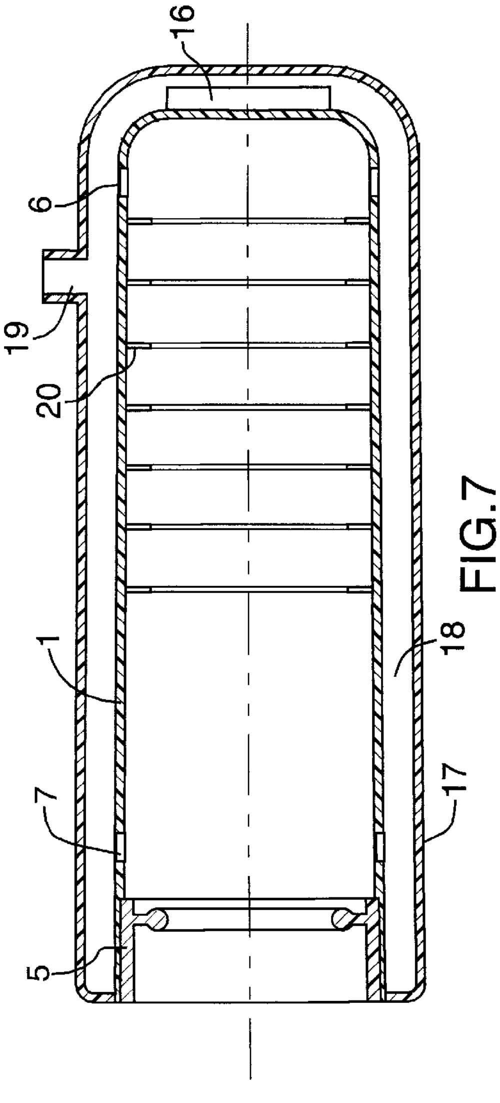
FIG. 7 is a longitudinal sectional view of a third embodiment including an exterior sheath for recirculating fluid and having internal annular baffles to increase fluid turbulence.

FIG. 7 illustrates a third embodiment of the invention having an external sheath 17 to form a fluid recirculating fluid jacket 18 between the exterior of the tubular housing 1 and the interior of the sheath 17. Inlet 6 and outlet 7 means, and the provision of an annular bushing 5 and vibrator 16 are the same as described above. A sheath inlet 19 provides for fresh fluid replacement, however the bulk of fluid flows in inlet 6 through the housing 1, out the outlet 7 into the fluid jacket 18 back to the inlet 6. To improve turbulence within the housing 1, annular baffles 20 are provided as an alternative to the corrugations of the housing 1 illustrated in FIGS. 1–6.

In summary then the invention provides a novel method of penile stimulation for use in the treatment of male impotence utilizing turbulent flow of fluid. The method comprises the following steps. Inserting the penis into a tubular housing 1, having internal walls, a closed forward end 2 and an open rearward end 3. The penis is submersed in fluid and disposed at a sufficient distance from the internal walls to permit fluid flow between the penis and the internal walls without frictional engagement. The user then pumps a flow of turbulent fluid between the penis and the internal walls in and out of the housing 1. Manually or mechanically operable pumping means are provided such as a small electric pump or fabricating the housing as a bellows.

Although the above description and accompanying drawings relate to specific preferred embodiments as presently contemplated by the inventor, it will be understood that the invention in its broad aspect includes mechanical and functional equivalents of the elements described and illustrated.

The embodiments of the invention in which an exclusive property or privilege is claimed are defined as follows:

1. A penile stimulation device for use in the treatment of male impotence utilizing turbulent flow of fluid, the device comprising:

tubular housing means, having internal walls, a closed forward end and an open rearward end, said rearward end having an opening means adapted for encircling the penil shaft, for housing the penis submersed in fluid and disposed at a sufficient distance from said internal walls to permit fluid flow between the penis and said internal walls; and pumping means mounted to the tubular housing and in flow communication with the housing internal walls, the pumping means adapted for conveying a flow of turbulent fluid between the penis and said internal walls in and out of the housing.

2. A device according to claim 1 wherein the opening means comprise removable bushing means adapted for sealingly engaging the shaft.

3. A device according to claim 1 wherein said pumping means includes fluid flow regulating means.

4. A device according to claim 3 wherein said regulating means comprise housing inlet means and outlet means each for one-way passage of fluid into and from the housing means respectively, at least one of said inlet and outlet means including a one way check valve.

5. A device according to claim 4 wherein said outlet means comprise an aperture and gate means for selectively impeding fluid flow through said aperture.

6. A device according to claim 5 comprising a plurality of apertures disposed radially through the housing adjacent the rearward end of the housing and said gate means comprise a sliding ring with an associated plurality of apertures.

7. A device according to claim 5 comprising a plurality of apertures disposed longitudinally through the rearward end of the housing and said gate means comprise a sliding disc with an associated plurality of apertures.

8. A device according to claim 1 wherein said pumping means is manually operable.

9. A device according to claim 8 wherein the housing means comprises a flexible bellows.

10. A device according to claim 1 wherein said pumping means includes a mechanically operable pump.

11. A device according to claim 10, wherein said mechanically operable pump includes a vibrator.

12. A device according to claim 1 wherein the internal walls of the housing means includes means for increasing fluid turbulence.

13. A device according to claim 12 wherein said means for increasing fluid turbulence comprise annular corrugations.

14. A device according to claim 12 wherein said means for increasing fluid turbulence comprise annular baffles.

15. A device according to claim 1 further comprising sheath means, disposed at a distance from the housing means, for enclosing said housing means, and forming a fluid recirculating jacket, the sheath means including a sheath inlet communicating with said jacket.

16. A method of penile stimulation for use in the treatment of male impotence utilizing turbulent flow of fluid, the method comprising:

inserting the penis into a tubular housing means, having internal walls, a closed forward end and an open rearward end, said rearward end having an opening means for encircling the penile shaft, for housing the penis submersed in fluid and disposed at a sufficient distance from said internal walls to permit fluid flow between the penis and said internal walls; and pumping a flow of turbulent fluid between the penis and said internal walls in and out of the housing.

17. A method according to claim 16 including regulating fluid flow.

18. A method according to claim 17 including the step of regulating fluid flow with a one way inlet valve and an outlet valve.

19. A method according to claim 16 wherein the housing means comprise a flexible bellows and the method includes the step of pumping fluid manually through reciprocal axial movement of the housing means relative to the penis.

20. A method according to claim 16 including the step of pumping fluid with mechanical means.

* * * * *